US012570649B2

(12) United States Patent
Bartos

(10) Patent No.: US 12,570,649 B2
(45) Date of Patent: Mar. 10, 2026

(54) ISAVUCONAZONIUM SALTS AND PROCESS FOR PREPARING THEREOF

(71) Applicant: Synthon B.V., Nijmegen (NL)

(72) Inventor: Petr Bartos, Blansko (CZ)

(73) Assignee: Synthon B.V., Nijmegen (NL)

( * ) Notice: Subject to any disclaimer, the term of this patent is extended or adjusted under 35 U.S.C. 154(b) by 1052 days.

(21) Appl. No.: 17/638,102

(22) PCT Filed: Aug. 17, 2020

(86) PCT No.: PCT/EP2020/072988
§ 371 (c)(1),
(2) Date: Feb. 24, 2022

(87) PCT Pub. No.: WO2021/037597
PCT Pub. Date: Mar. 4, 2021

(65) Prior Publication Data
US 2022/0289735 A1 Sep. 15, 2022

(30) Foreign Application Priority Data
Aug. 26, 2019 (EP) .................................... 19193584

(51) Int. Cl.
*A61K 31/4439* (2006.01)
*C07D 417/14* (2006.01)

(52) U.S. Cl.
CPC .................................. *C07D 417/14* (2013.01)

(58) Field of Classification Search
CPC ............................... C07D 417/14; A61P 31/10
See application file for complete search history.

(56) References Cited

FOREIGN PATENT DOCUMENTS

| | | | | |
|---|---|---|---|---|
| CN | 105420306 | | 3/2016 | |
| CN | 105420306 A | * | 3/2016 | .............. C12P 17/10 |
| CN | 106916152 | | 7/2017 | |
| CN | 106916152 A | * | 7/2017 | ........... C07D 417/14 |
| WO | WO2001032652 | | 5/2001 | |
| WO | WO-2016016766 A2 | * | 2/2014 | ........... C07D 417/14 |
| WO | WO2016/016766 | | 2/2016 | |

* cited by examiner

*Primary Examiner* — Jeffrey S Lundgren
*Assistant Examiner* — Paul Randall Gauger
(74) *Attorney, Agent, or Firm* — Buscher Patent PLLC

(57) ABSTRACT

The present invention relates to the process of preparation of salts of compound of formula (1).

(1)

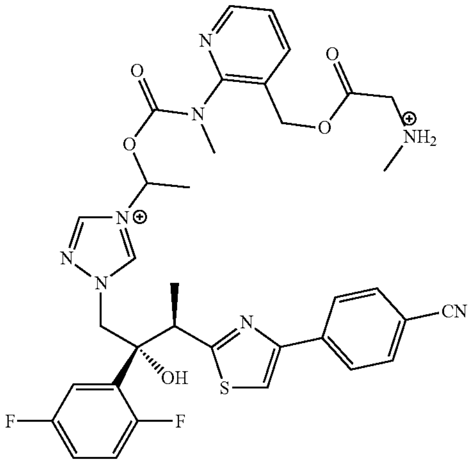

18 Claims, No Drawings

ISAVUCONAZONIUM SALTS AND PROCESS FOR PREPARING THEREOF

BACKGROUND OF THE PRESENT INVENTION

This invention relates to salts of compound (1) and processes for preparation thereof:

(1)

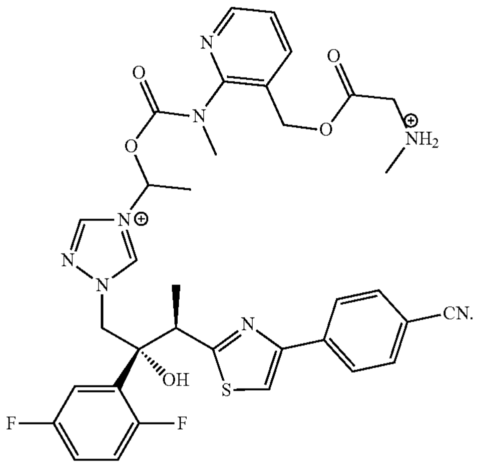

Isavuconazonium sulfate, N-Methylglycine [2-[N-[1-[1-[(2R,3R)-3-[4-(4-cyanophenyl)-2-thiazolyl]-2-(2,5-difluorophenyl)-2-hydroxybutyl]-1H-1,2,4-triazolium-4-yl] ethoxy]carbonyl]-N-methylamino]-3-pyridinyl]methyl ester sulfate, is a prodrug of Isavuconazole. Isavuconazonium sulfate was launched for oral and intravenous treatment of invasive aspergillosis and invasive mucormycosis. Isavuconazonium sulfate was disclosed in WO2001032652 application. The application also describes a process for preparation of Isavuconazonium dihydrochloride, compound of following structure:

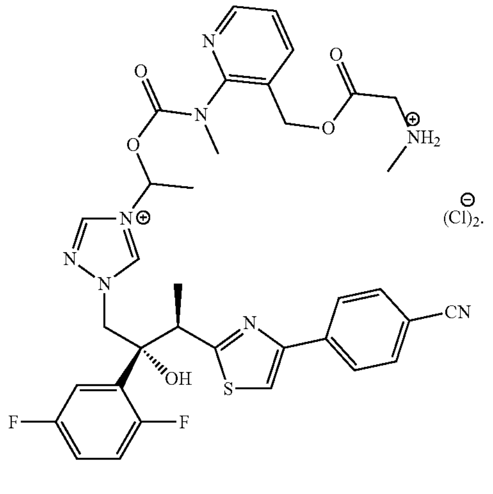 [SMILES: C[NH2+]CC(=O)OCc1cccnc1N(C)C(=O)OC(C)[n+]1cnn(C[C@](O)(c2cc(F)ccc2F)[C@@H](C)c2nc(-c3ccc(C#N)cc3)cs2)c1 ; "(Cl)2."]

CN105420306 and CN106916152 applications disclose process for preparation of Isavuconazonium sulfate, compound of following structure:

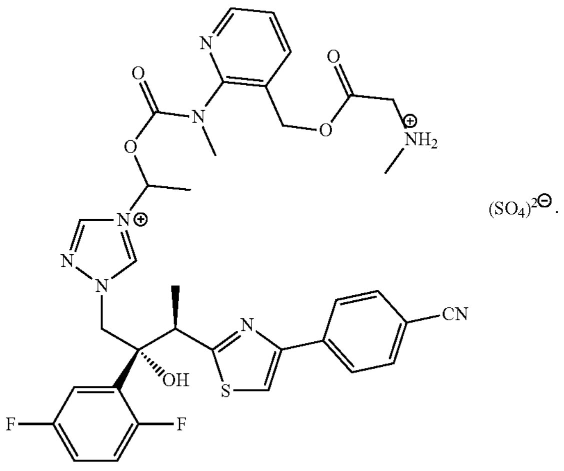 [SMILES: C[NH2+]CC(=O)OCc1cccnc1N(C)C(=O)OC(C)[n+]1cnn(C[C@](O)(c2cc(F)ccc2F)[C@@H](C)c2nc(-c3ccc(C#N)cc3)cs2)c1]

The salts of compound of formula (1) disclosed in the prior art are soluble in water. The isolation of the salts requires lyophilisation. Lyophilisation is a technique that it energetically demanding and not very suitable for high scale production. The processes disclosed in the prior art also comprise chromatographic purifications and ion exchange chromatography for ion exchanges. Both these techniques are not suitable for higher scale production.

Therefore, there is a need for alternative process that does not comprise chromatographic purification, ion exchange chromatography and lyophilisation and that provides salts of compound of formula (1) in sufficient purity and yield.

BRIEF DESCRIPTION OF THE INVENTION

The presented invention relates to a process for preparation of a salt of compound of formula (1) comprising:

(1)

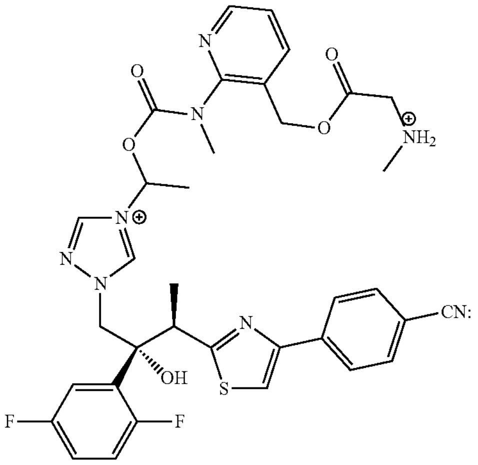

a. Reacting compound of formula (2) with a first acid $HA_1$ to obtain compound (3):

(2)

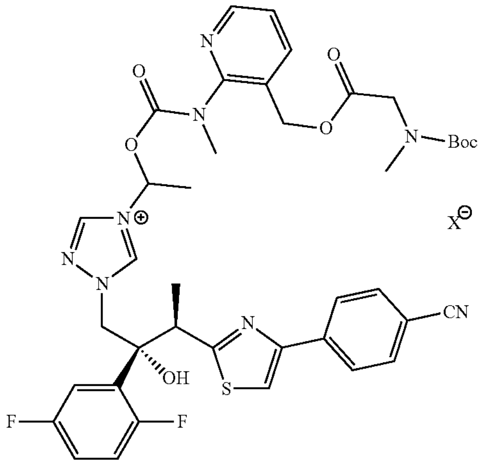

(3)

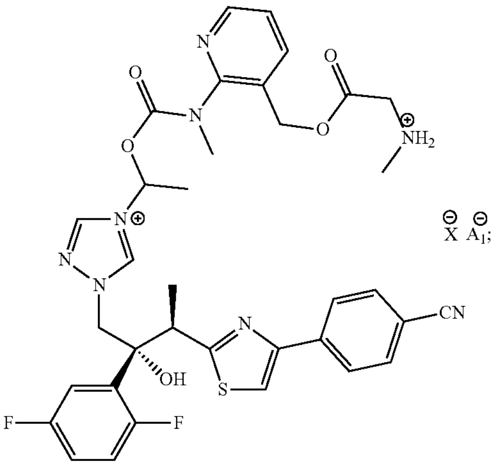

Boc:

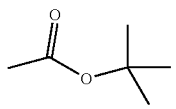

X means Cl or Br or I $A_1^-$ means an anion originated from the first acid $HA_1$;

b. Reacting compound of formula (3) with a second acid $HA_2$ in a water immiscible solvent to obtain a mixture comprising compound (4) in the water immiscible solvent:

(4)

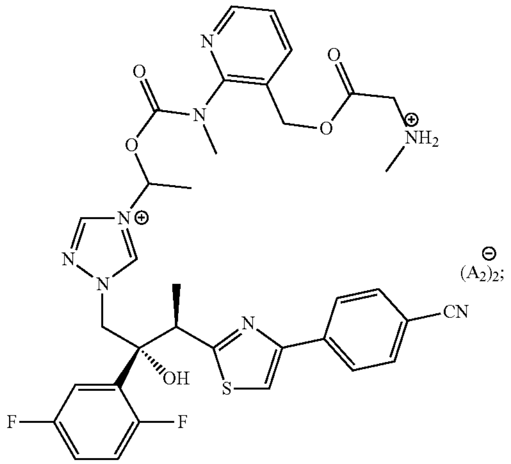

$A_2^-$ means an anion originated from the second acid $HA_2$.

The presented invention further relates to a process for preparation of Isavuconazonium sulfate, i.e. compound of formula (10), comprising reacting compound of formula (9) with $Ba^{2+}$ base:

(9)

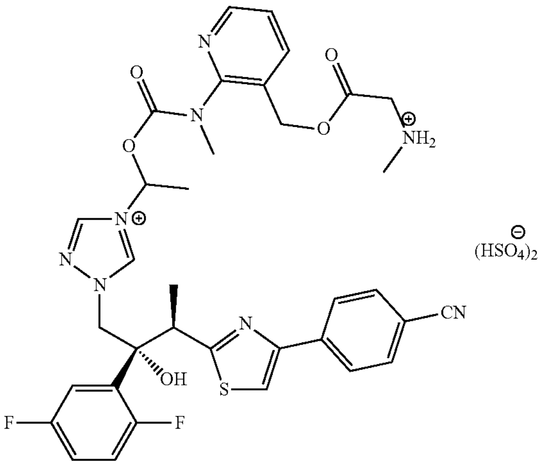

(10)

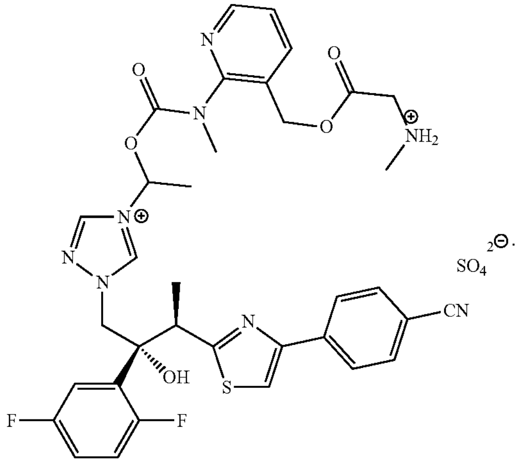

The invention also relates to salts of compound of formula (1) with an acid $HA_2$ of formula $CX_3(CX_2)_mCOOH$, m is between 0 and 7 and X is selected from H or Cl or F and solid forms thereof.

The invention also relates to a process comprising transformation of a to salts of compound of formula (1) with an acid $HA_2$ of formula $CX_3(CX_2)_mCOOH$, m is between 0 and 7 and X is selected from H or Cl or F to a different salt insoluble in a water immiscible solvent.

The invention further relates to pharmaceutical composition comprising the salts of compound of formula (1).

The presented process does not comprise chromatographic purification, ion exchange chromatography or lyophilisation and provides salts of compound of formula (1) in good purity and yield. The salts of formula (1) with an acid $HA_2$ of formula $CX_3(CX_2)_mCOOH$, m is between 0 and 7 and X is selected from H or Cl or F are soluble in a water immiscible solvent and can be isolated without using lyphilization technique by simple distilling off the solvent. They can be also transformed into a different salt of compound of formula (1), for example the salts disclosed in the prior art that are insoluble in a water immiscible solvent and can be isolated by precipitation without a need of lyophilization.

DETAILED DESCRIPTION OF THE INVENTION

The presented invention relates to a process for preparation of a salt of compound of formula (1) comprising:

(1)

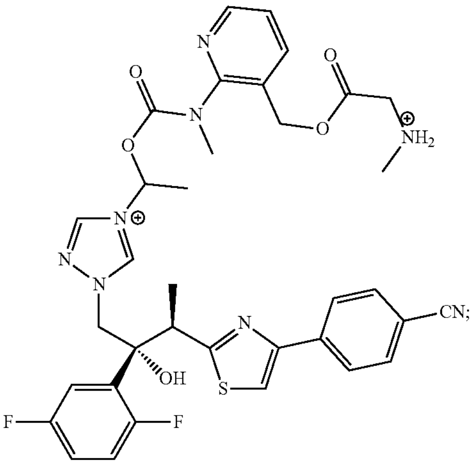

a. Reacting compound of formula (2) with a first acid $HA_1$ to obtain compound (3):

(2)

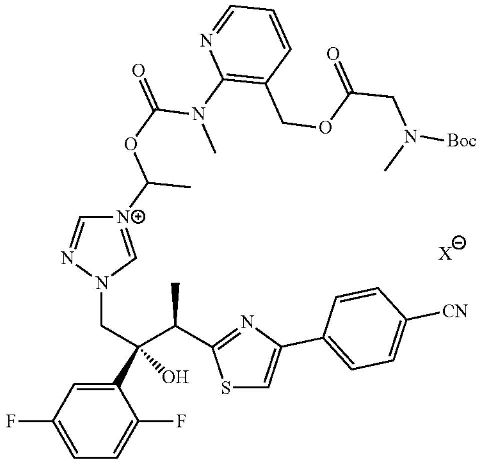

(3)

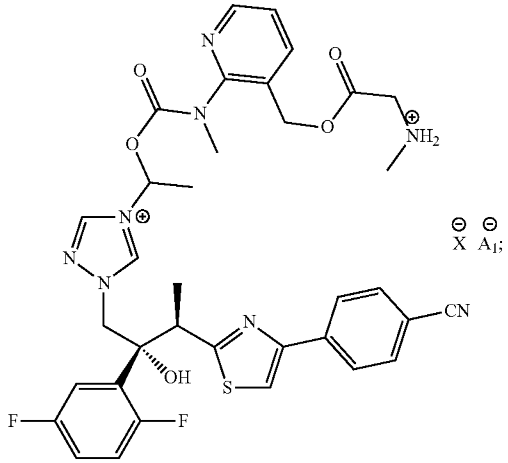

X means Cl or Br or I;

$A_1^-$ means an anion originated from the first acid $HA_1$;

b. Reacting compound of formula (3) with a second acid $HA_2$ in a water immiscible solvent to obtain a mixture comprising compound (4) in the water immiscible solvent:

(4)

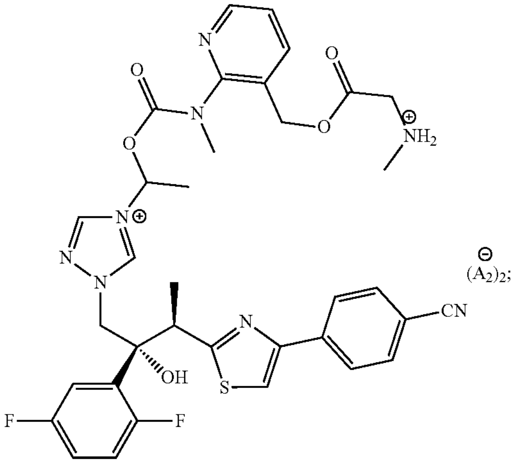

$A_2^-$ means an anion originated from the second acid $HA_2$.

The salt of compound of formula (1) is preferably a salt with an acid of formula $CX_3(CX_2)_mCOOH$, m is between 0 and 7 and X is selected from H or Cl or F, preferably the salt is $CF_3COOH$.

Boc group in the compound of formula (2) can be substituted by any nitrogen protective group that can be deprotected by an acid in an anhydrous solvent.

In comparison with the prior art salts the salts of formula (1) with an acid of formula $CX_3(CX_2)_mCOOH$, m is between 0 and 7 and X is selected from H or Cl or F are soluble in a water immiscible solvent and can be isolated without using lyphilization technique by simple distilling off the solvent. They can be also transformed into a different salts of compound of formula (1), for example the salts disclosed in the prior art that are insoluble in a water immiscible solvent and can be isolated by precipitation without a need of lyophilization.

The mixture of compound of formula (2) in a water immiscible solvent can be extracted with a water solution of an acid having pH between 1 and 6, preferably between 2 and 5, more preferably between 3 and 4, and ionic strength between 0.5 mol/l and 2 mol/l before reacting in step a. The acid can be selected from $H_3PO_4$ or formic acid or acetic acid or citric acid, preferably it is $H_3PO_4$. The extraction can be optionally repeated for example twice or three times. In the prior art processes compound of formula (2) is extracted with ethyl acetate and water. The disadvantage of the procedure is strong foaming of the mixture that causes troubles in high scale production. The foaming of the mixture is suppressed when a water solution of an acid having pH between 1 and 6, preferably between 2 and 5, more preferably between 3 and 4, and ionic strength between 0.5 mol/l and 2 mol/l is used for extraction. The second advantage of the extraction process using a water solution of an acid having pH between 1 and 6, preferably between 2 and 5, more preferably between 3 and 4, and ionic strength between 0.5 mol/l and 2 mol/l is that it further improves the purity of obtained compound (2).

The water immiscible solvent can be selected from selected an acetate (such as methyl acetate or ethyl acetate or propyl acetate or isopropyl acetate or butyl acetate) or an alkane (such as pentane or hexane or heptane) or an ether (such as dimethyl ether or diethyl ether or methyl tert butyl ether) or toluene or halogenated alkane (such as dichloromethane), preferably it is an acetate, more preferably ethyl acetate or isopropyl acetate. Compound (2) is dissolved in the water immiscible solvent. The concentration of the compound (2) in the solvent can be between 1-50% (wt %).

The mixed organic layer is dried over for example anhydrous $MgSO_4$. The resulting solution can be optionally concentrated or can be used as a solution in the subsequent step.

The ionic strength, I, of a solution is a function of the concentration of all ions present in that solution that can be calculated:

$$I = \frac{1}{2}\sum_{i=1}^{n} c_i\, z_i^2$$

$c_i$ is the molar concentration of ion i (mol/l), $z_i$ is the charge number of that ion, and the sum is taken over all ions in the solution.

In the step a. of the process of the invention compound of formula (2) is reacted with a first acid $HA_1$ to obtain compound (3):

(2)

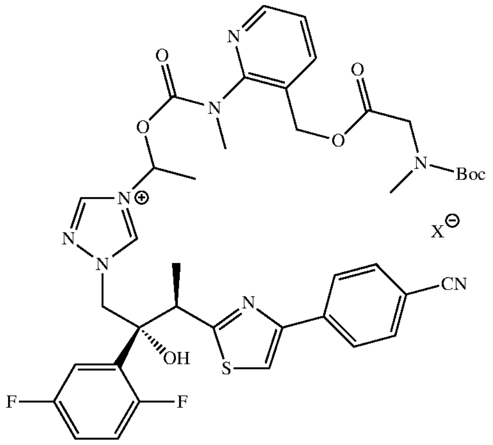

(3)

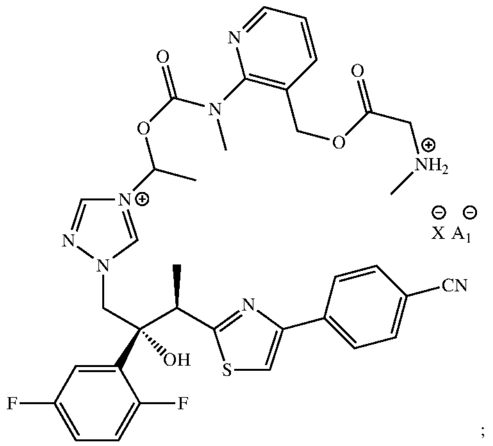

;

X means Cl or Br or I;

$A_1^-$ means an anion originated from the first acid $HA_1$.

The first acid $HA_1$ can be selected from a strong mineral acid such as HCl or HBr or HI, preferably it is HCl. The molar ration of the compound (2) and the acid $HA_1$ can be between 1:10 and 1:20, preferably it is between 1:12 and 1:16. The reaction can be performed in a suitable solvent such as an acetate (such as methyl acetate or ethyl acetate or propyl acetate or isopropyl acetate or butyl acetate) or an alkane (such as pentane or hexane or heptane) or an ether (such as dimethyl ether or diethyl ether or methyl tert butyl ether) or toluene or an halogenated alkane (such as dichloromethane), preferably it is an acetate, more preferably ethyl acetate or isopropyl acetate. The concentration of the compound (2) in the solvent can be between 1-50% (wt %), preferably it is 10% (wt %). The strong mineral acid $HA_1$ can be added to the solution of compound (2) in the solvent or the solution of compound (2) in a solvent is added to the strong mineral acid $HA_1$. The strong mineral acid $HA_1$ can be used in a form of a solution in a solvent or can be used without solvent. The addition can be performed in a course of between 30 and 240 minutes at between −20° C. and 10° C. The reaction is performed at between −20° C. and 10° C. for between 30 and 240 minutes. The reaction mixture is filtrated, the filtration cake can be washed with the solvent and the solid compound (3) can be dried. In a preferred embodiment when $HA_1$ is hydrochloric acid and X is I, the compound (3) is compound of following formula (3a):

(3a)

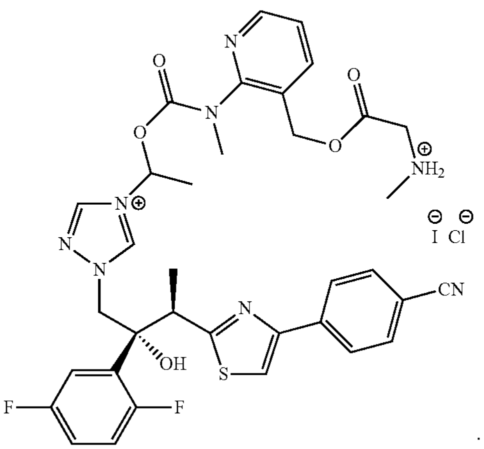

The compound (2) can be prepared of the process disclosed in WO2001032652 application or by a process comprising reacting compound (7) with compound (8) in a suitable solvent, for example acetonitrile, in a presence of NaI:

(7)

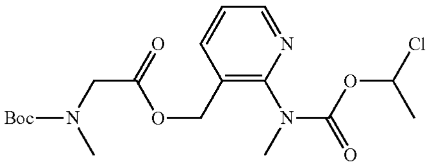

(8)

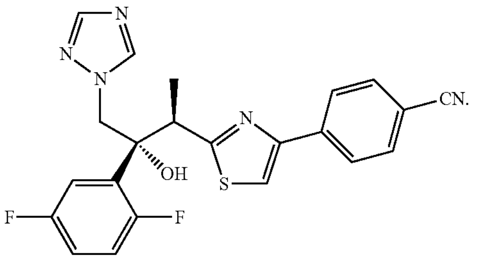

The concentration of compound (7) in the solvent can be between 0.05 and 0.3 g/ml, preferably it is between 0.1 and 0.25 g/ml. The molar ratio between compound (7) and (8) can be between 1.2:1 and 1.8:1. The molar ratio between compound (7) and NaI can be between 1:1 and 1:1.5. The reaction is performed under a protective atmosphere, for example using argon or nitrogen. The reaction is performed at a temperature between 40° C. and 80° C. for between 2 and 24 hours The reaction progress can be monitored by any suitable technique, for example HPLC or GPC. Compounds (7) and (8) are commercially available or can be prepared by a process disclosed in WO2001032652.

Compound of formula (3) is subsequently reacted with a second acid $HA_2$ in a water immiscible solvent to obtain a mixture comprising compound (4) in the water immiscible solvent:

(4)

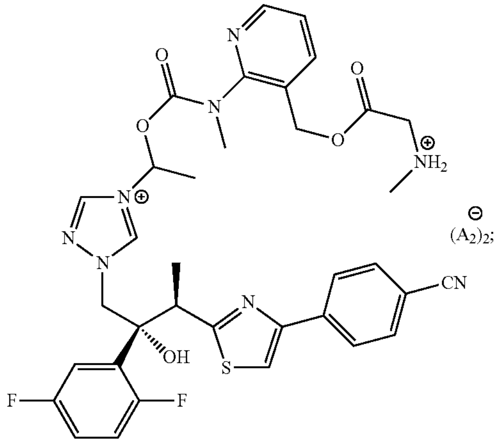

$A_2^-$ means an anion originated from the first acid $HA_2$.

The water immiscible solvent can be selected from an acetate (such as methyl acetate or ethyl acetate or propyl acetate or isopropyl acetate or butyl acetate) or an alkane (such as pentane or hexane or heptane) or an ether (such as dimethyl ether or diethyl ether or methyl tert-butyl ether) or toluene or a halogenated alkane (such as dichloromethane), preferably it is an acetate, more preferably isopropyl acetate or ethyl acetate.

The compound of formula (3) is dissolved in a suitable solvent such as water. The solution is reacted with a second acid $HA_2$ dissolved in a water immiscible solvent. The $HA_2$ can be an acid of general formula $CX_3(CX_2)_mCOOH$, m is between 0 and 7 and X is selected from H or Cl or F, preferably it is $CF_3COOH$.

The molar ratio between compound (3) and the acid $HA_2$ can be between 1:5 and 1:20, preferably it is between 1:10 and 1:15. The concentration of compound (3) in the solvent can be between 1 and 50% (wt %), preferably it is 10% (wt %). The reaction can be performed at between 0 and 25° C. for between 1 and 10 hours.

In a preferred embodiment when $HA_2$ is trifluoroacetic acid ($CF_3COOH$), the compound (4) is compound of following formula (4a)

(4a)

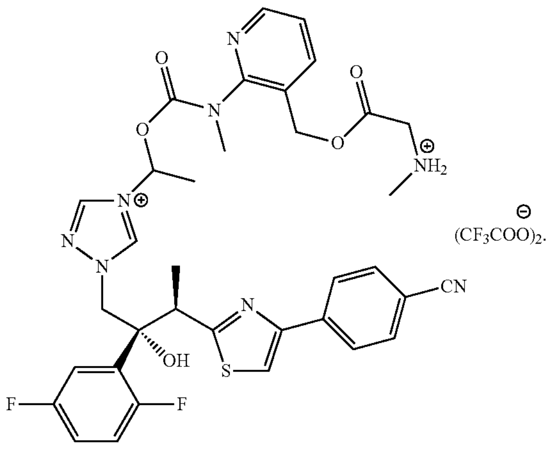

After the reaction is finished, to the mixture of compound (4) in a water immiscible solvent water is added. The pH of the mixture is set between 1 and 6, preferably between 2 and 5, more preferably between 4 and 5. The second possibility is that the pH of used water is set so that pH of the mixture after addition of water is between 1 and 6, preferably between 2 and 5, more preferably between 4 and 5. pH is set by for example a suitable base such as a carbonate (such as lithium or sodium or potassium or calcium carbonate) or a hydrogen-carbonate (such as lithium or sodium or potassium or calcium hydrogencarbonate), preferably by a hydrogen-carbonate, more preferably by sodium hydrogen carbonate. The volume ratio between water and the water immiscible solvent used for dissolving the acid $HA_2$ can be between 1:1 and 1:3, preferably it is between 1:1.5 and 1:2.5 The extraction can be repeated, for example twice or three times. The mixed organic layer is dried for example with a molecular sieve or $MgSO_4$ for example overnight. The dried solution can be evaporated to provide solid compound (4) or it can be used in a form of a solution in the subsequent step. Compound of formula (4) can be used for preparation of a different salt of compound of formula (1), for example salts disclosed in the prior art. Compound (4) is dissolved in a water immiscible solvent. Because these different salts are insoluble in the water immiscible solvent they can be isolated from the mixture by precipitating and filtrating the mixture without a need of lyophilization.

To prepare the different salts of compound (1), the compound (4) is contacted in a water immiscible solvent with a third acid $HA_3$, wherein $pK_a$ of $HA_3<pK_a$ of $HA_2$. The third acid $HA_3$ can be selected for example from $H_2SO_4$ or HCl or HBr or $H_3PO_4$, preferably it is $H_2SO_4$. The solvent can be selected from for example from an acetate (such as methyl acetate or ethyl acetate or propyl acetate or isopropyl acetate or butyl acetate) or an alkane (such as pentane or hexane or heptane) or an ether (such as dimethyl ether or diethyl ether or methyl tert butyl ether) or toluene or a halogenated alkane (such as dichloromethane), preferably it is an acetate, more preferably isopropyl acetate or ethyl acetate. The concentration of compound (4) in the solvent can be between 0.15 g/ml and 0.6 g/ml, preferably it is between 0.2 g/ml and 0.5 g/ml. The compound (4) is dissolved in the solvent and the mixture is cooled to a temperature between −30° C. and 25° C. The acid $HA_3$ can be added either in solution in the solvent or as a solid. The molar ratio between compound (4) and the acid $HA_3$ can be between 1:1 and 1:2.2. The acid $HA_3$ is added at a temperature between −30° C. and 25° C. and the mixture is stirred at the same temperature for between 1 and 5 hours, preferably for between 2 and 3 hours. The mixture can be warmed to a temperature for example between 2° and 25° C. and the mixture is filtrated. The solid is dried to provide the salt of compound (1) with an acid $HA_3$.

In a preferred embodiment when $HA_3$ is sulphuric acid ($H_2SO_4$), the salt of compound (1) is compound of following formula (9):

(9)

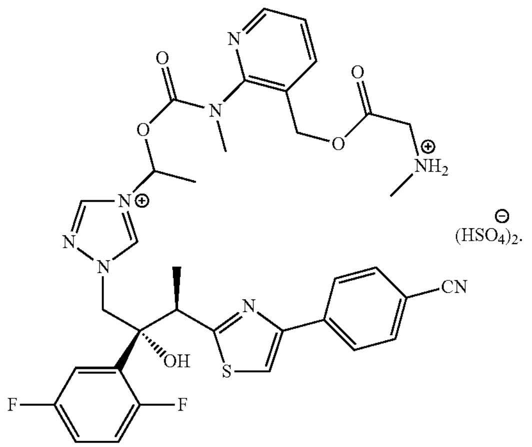

It was also surprisingly found that use of the presented transformation of compound (4) into a different salt of compound of formula (1) can significantly increase the purity of the salt of formula (1).

The compound (9) can be further transformed into Isavuconazonium sulfate, compound (10):

(10)

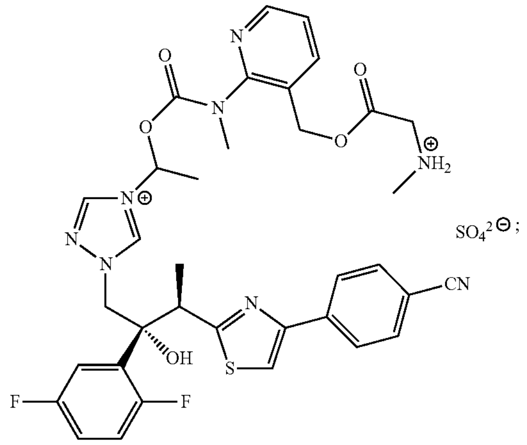

by a process comprising reacting compound of formula (9) with $Ba^{2+}$ base. $Ba^{2+}$ base can be selected from $Ba(OH)_2$ or $Ba(acetate)_2$ or $Ba(formate)_2$, preferably it is $Ba(acetate)_2$. The advantage for using a weak base such as $Ba(acetate)_2$ is formation of lower amount of impurities. The molar ratio between compound of formula (9) and $Ba^{2+}$ base can be between 1:1 and 1:1.2. The reaction can be performed in a suitable solvent, for example water or a mixture of water and a water miscible solvent such as an alcohol (such as methanol or ethanol or propanol) or acetonitrile or acetic acid. Concentration of compound (9) in the solvent can be between 0.05 g/ml and 0.15 g/ml, preferably between 0.07 g/ml and 0.1 g/ml. Compound (9) is dissolved in the solvent and the mixture is cooled to a temperature between −20° C. and 20° C., preferable between 0° C. and 10° C. A solution of the $Ba^{2+}$ base in the solvent is added at this temperature in the course of between 20 and 240 minutes, preferably between 30 and 90 minutes. The mixture is stirred at this temperature for between 60 and 180 minutes. The mixture is filtrated and the filtrate is concentrated to provide compound of formula (10), Isavuconazonium sulfate, in good yield and purity.

The salts of compound of formula (1) can be used in a pharmaceutical composition for the treatment of conditions treatable by Isavuconazonium sulfate or Isavuconazole.

The invention will be further described with reference to the following examples.

EXAMPLES

Example 1: Compound 2 (X: I)

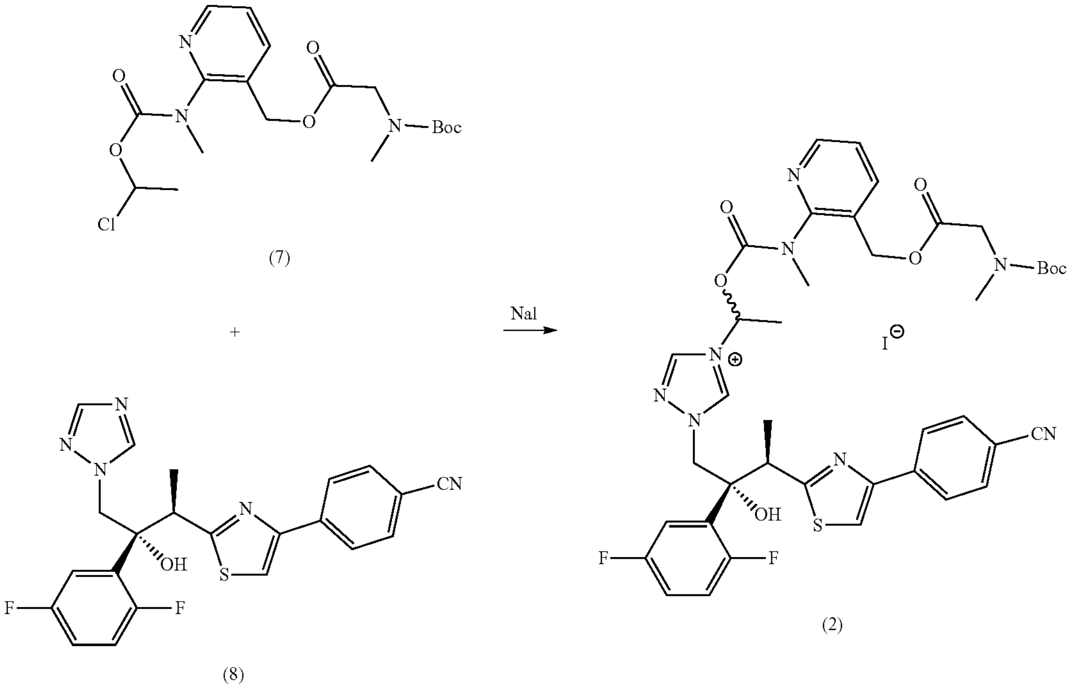 [SMILES: C[C@@H](c1nc(-c2ccc(C#N)cc2)cs1)[C@](O)(Cn1cncn1)c1cc(F)ccc1F ; CC(Cl)OC(=O)N(C)c1ncccc1COC(=O)CN(C)C(=O)OC(C)(C)C ; CC(OC(=O)N(C)c1ncccc1COC(=O)CN(C)C(=O)OC(C)(C)C)[n+]1cnn(C[C@](O)(c2cc(F)ccc2F)[C@@H](C)c2nc(-c3ccc(C#N)cc3)cs2)c1 ; [I-]]

(7) + (8) → (2)

39.9 g of compound (7), 30.0 g of compound (8), 14.39 g of NaI were mixed with 300 ml of acetonitrile. The mixture was stirred under argon at 45° C. for 19 hours to produce a yellow suspension. The reaction mixture was filtered and evaporated at 40° C. under reduced pressure. The evaporation residue was dissolved in 300 ml of ethyl acetate. The solution was washed three times with a water solution of $H_3PO_4$ (PH=3, ionic strength 0.5 mol/l). No foaming of the mixture appeared. The organic phase was dried over anhydrous $MgSO_4$ and filtered to produce a stock solution of compound (2), X: I in 90% of purity (HPLC). Following the procedure disclosed in Example 1 the extraction was also tested with a water solution of $H_3PO_4$ (pH=3, ionic strength 1.5 mol/l, pH 4 ionic strength 2, pH 5 ionic strength 1.5. No foaming of the mixture appeared in all cases.).

Example 2: Compound 3a

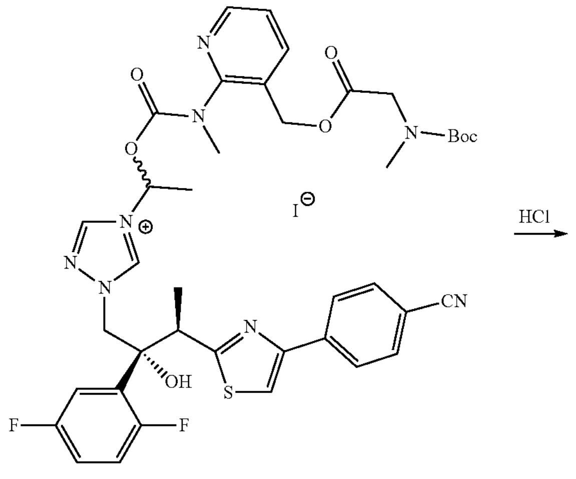

(2)

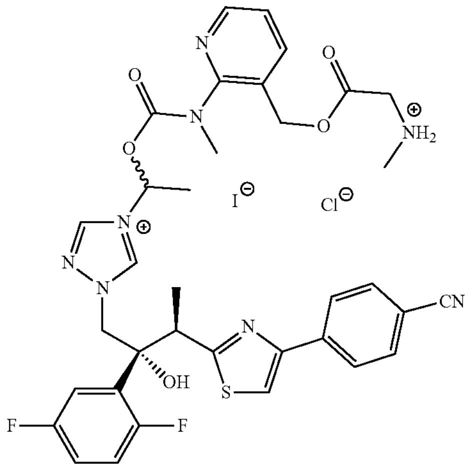

(3a)

The stock solution prepared according to Example 1 was added dropwise to a stirred 199 g solution of HCl (10% solution in ethyl acetate) cooled to 0° C. over 2 hours. The mixture was stirred for additional 1 hour at the same temperature. The solids were collected by filtration and the filter cake was washed with 250 ml of EtOAc. The product was dried in a vacuum-oven (100 torr, 25° C., under $N_2$) for 15 h to provide the product in almost quantitative yield and 93% purity (HPLC).

Example 3: Compound 4a

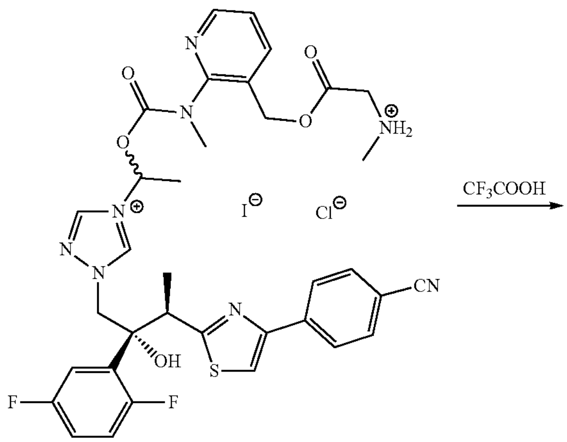

(3a)

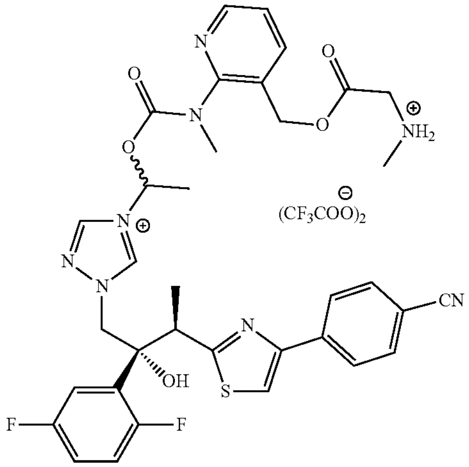

(4a)

The solid compound 3a prepared according to Example 2 was dissolved in 400 ml of water. The solution was washed with 3×400 ml of ethylacetate. The water mixture was mixed with 750 ml i-PrOAc (750 ml) and 47 ml of trifluoroacetic acid ($CF_3COOH$). The organic layer was separated and mixed with 400 ml of water. pH of the mixture was set to pH 4.3 using solid $NaHCO_3$. The organic layer was separated and dried with a molecular sieve overnight. The HPLC purity of the product in solution was 99% (HPLC). The dried extract was evaporated (25° C.) under reduced pressure to produce 29.54 g of solid compound 4a, purity 92% (HPLC).

Example 4: Compound 9

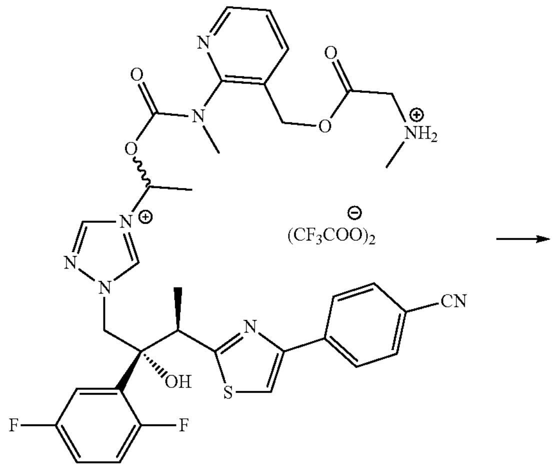

(4a)

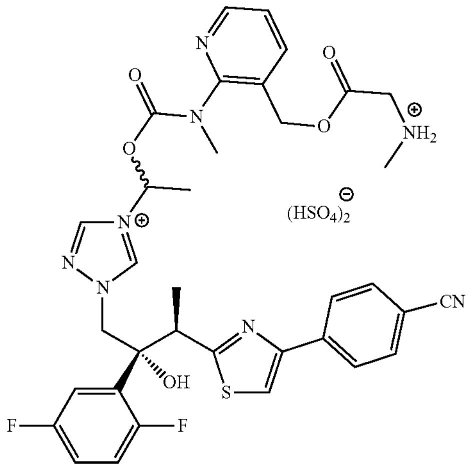

(9)

The 29.5 g of compound (4a) with purity 92% (HPLC) was dissolved in 105.5 ml of isopropyl acetate. The mixture was cooled to −17° C. Solution of 3.5 ml of sulphuric acid in 170 ml of isopropyl acetate was added dropwise over 2 h. The suspension was allowed to warm up to 25° C. and the precipitated solid was collected by filtration. The product was dried in a vacuum-oven (100 torr, 22-25° C., under $N_2$) for 18 hours to produce 25.8 g of solid compound (9) (90% yield, 97% HPLC purity).

Example 5: Compound 10

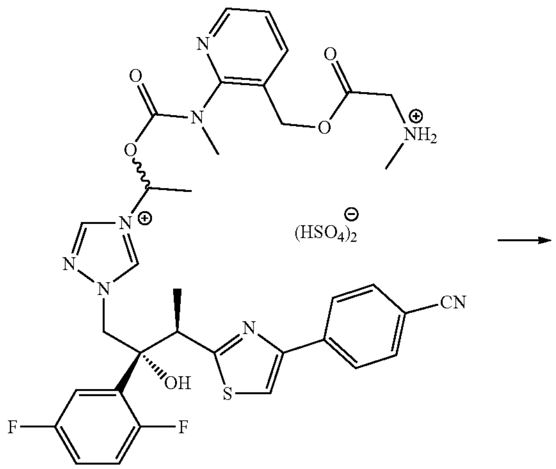

(9)

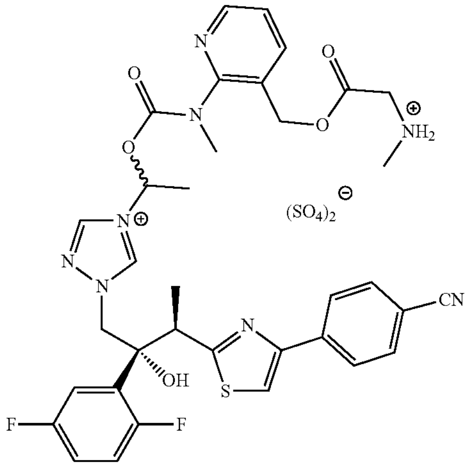

(10)

0.25 g of compound of formula (9) was dissolved in 0.5 ml water and the solution was stirred at 7° C. for 15 minutes. The solution of 0.068 g of barium acetate in 1 ml of water was added dropwise during 0.25 h. The mixture was stirred at 7° C. for 1.5 h. The fine precipitate ($BaSO_4$) was formed and filtered off to produce aqueous solution of Isavuconazonium sulphate containing 97% of the product (HPLC).

The invention claimed is:

1. A process for preparation of a salt of compound of formula (1) comprising:

(1)

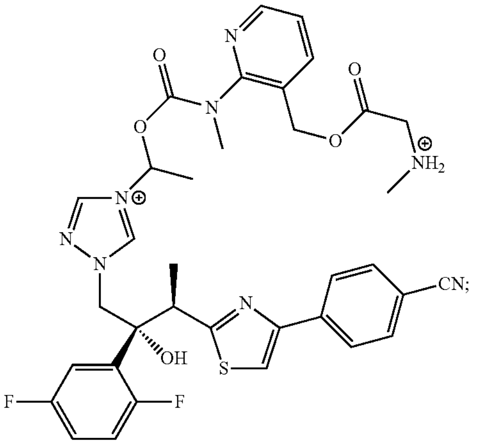

a) reacting compound of formula (2) with a first acid $HA_1$ to obtain compound (3):

(2)

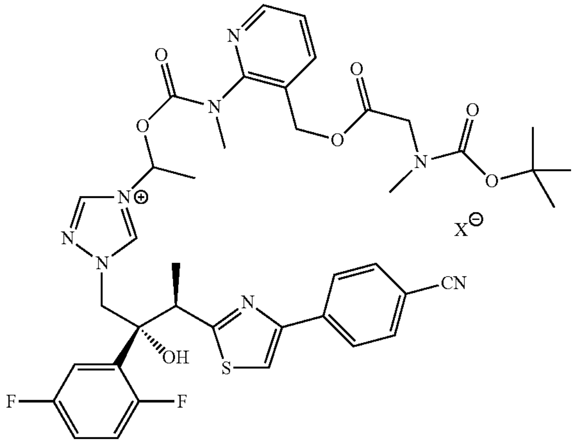

(3)

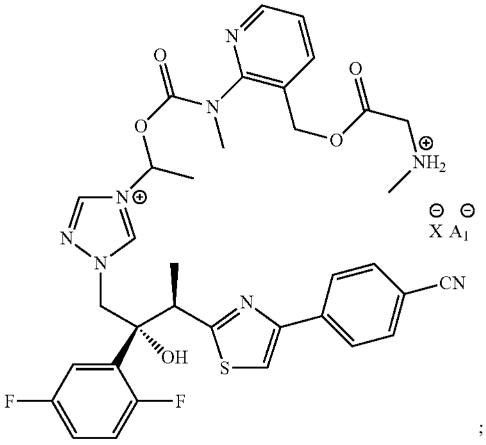

;

X means Cl or Br or I;

$A_1^-$ means an anion originated from the first acid $HA_1$;

b) reacting compound of formula (3) with a second acid $HA_2$ in a water immiscible solvent to obtain a mixture comprising compound (4) in the water immiscible solvent:

(4)

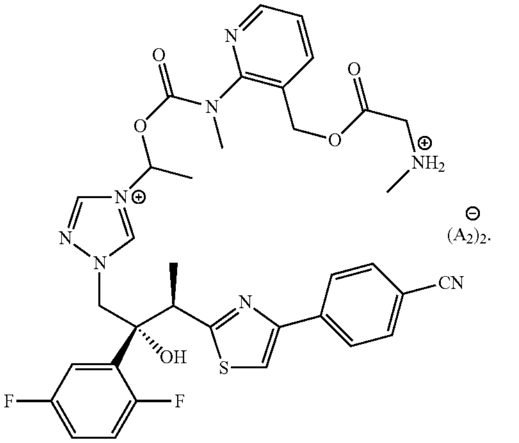

$A_2^-$ means an anion originated from the second acid $HA_2$.

2. The process according to claim 1 wherein the salt of compound of formula (1) is a salt with an acid of formula $CX_3(CX_2)_mCOOH$, m is between 0 and 7 and X is selected from H or Cl or F.

3. The process according to claim 2 wherein the acid is $CF_3COOH$.

4. The process according to claim 1 wherein a solution comprising water immiscible solvent and compound of formula (2) is extracted with a water solution of an acid having pH between 1 and 6 and ionic strength between 0.5 mol/l and 2 mol/l before reacting in step a).

5. The process according to claim 4 wherein the acid is selected from $H_3PO_4$ or formic acid or acetic acid or citric acid.

6. The process according to claim 1 wherein the water immiscible solvent in step b) is selected from an acetate or an alkane or an ether or toluene or a halogenated alkane.

7. The process according to claim 1 wherein the process further comprises extracting of the mixture obtained in step b) with water at pH between 1 and 6.

8. The process according to claim 1 wherein the first acid $HA_1$ is selected from HCl or HBr or HI.

9. The process according to claim 1 wherein the second acid $HA_2$ is $CX_3(CX_2)_mCOOH$, m is between 0 and 7 and X is selected from H or Cl or F.

10. The process according to claim 1 further comprising contacting the compound (4) in a water immiscible solvent with a third acid $HA_3$ wherein $pK_a$ of $HA_3 < pK_a$ of $HA_2$ to obtain a salt of compound of formula (1) with $HA_3$.

11. The process according to claim 10 wherein the third acid $HA_3$ is selected from $H_2SO_4$ or HCl or HBr or $H_3PO_4$.

12. The process according to claim 10 wherein the third acid $HA_3$ is $H_2SO_4$ and the salt of compound of formula (1) is compound of formula (9):

(9)

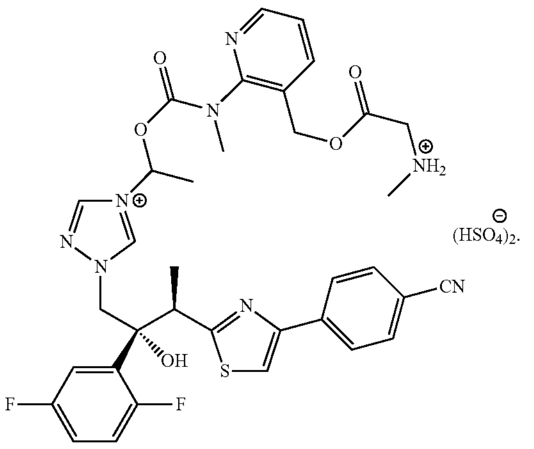

13. The process according to claim 12 further comprising contacting the compound of formula (9) with $Ba^{2+}$ base to obtain compound of formula (10), Isavuconazonium sulfate:

(10)

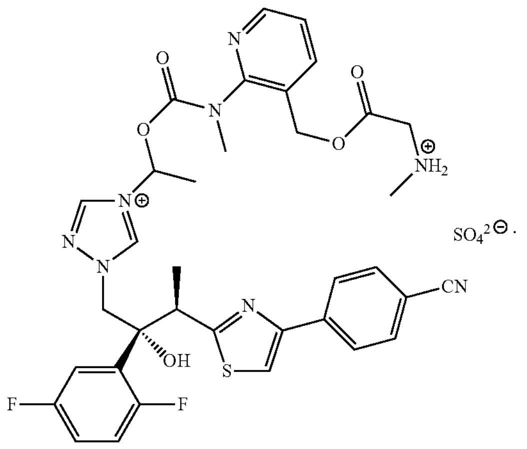

14. A process for purification a salt of compound of formula (1) comprising contacting the compound (4)

(4)

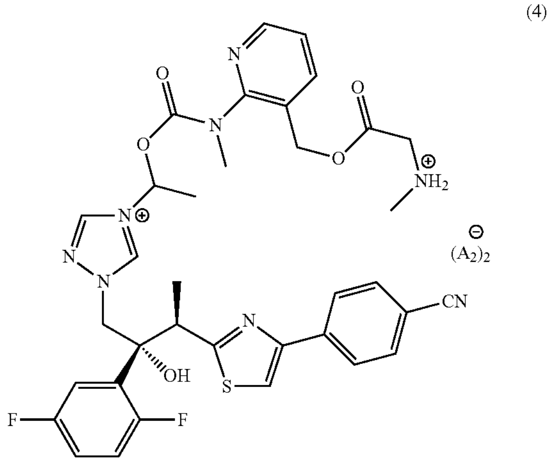

wherein $A_2^-$ means an anion originated from an acid $HA_2$, in a water immiscible solvent with an acid $HA_3$ wherein $pK_a$ of $HA_3$<$pK_a$ of $HA_2$ to obtain a salt of compound of formula (1) with $HA_3$ (1)

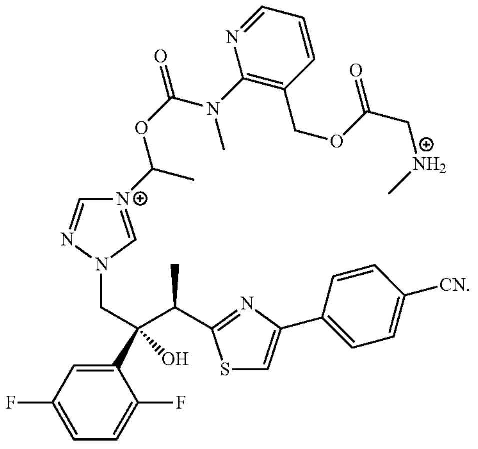

15. The process according to claim 14 wherein compound (4) is a salt of compound (1) with an acid of formula $CX_3(CX_2)_mCOOH$, m is between 0 and 7 and X is selected from H or Cl or F.

16. A salt of compound of formula (1)
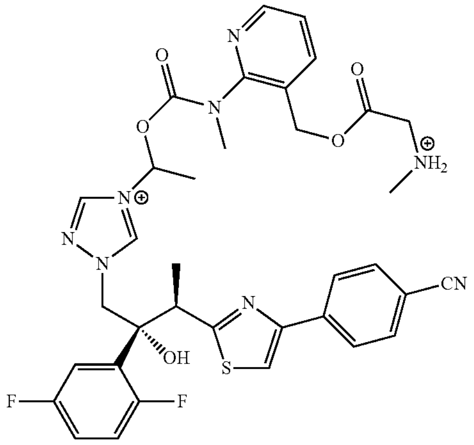
(1)
with an acid of formula $CX_3(CX_2)_mCOOH$, m is between 0 and 7 and X is selected from H or Cl or F.
17. A solid form of the salt of claim 16.
18. A pharmaceutical composition comprising the salt according to claim 16.
* * * * *